(12) United States Patent
Quellec et al.

(10) Patent No.: US 10,062,164 B2
(45) Date of Patent: Aug. 28, 2018

(54) METHOD FOR THE ANALYSIS OF IMAGE DATA REPRESENTING A THREE-DIMENSIONAL VOLUME OF BIOLOGICAL TISSUE

(71) Applicant: MIMO AG, Bern (CH)

(72) Inventors: Gwenolé Quellec, Brest (FR); Jens Kowal, Seftigen (CH); Peter Maloca, Lucerne (CH)

(73) Assignee: MIMO AG, Bern (CH)

( * ) Notice: Subject to any disclaimer, the term of this patent is extended or adjusted under 35 U.S.C. 154(b) by 56 days.

(21) Appl. No.: 15/302,390

(22) PCT Filed: Mar. 30, 2015

(86) PCT No.: PCT/CH2015/000049
§ 371 (c)(1),
(2) Date: Oct. 6, 2016

(87) PCT Pub. No.: WO2015/154200
PCT Pub. Date: Oct. 15, 2015

(65) Prior Publication Data
US 2017/0032522 A1 Feb. 2, 2017

(30) Foreign Application Priority Data

Apr. 7, 2014 (CH) ........................ 0536/14

(51) Int. Cl.
*G06K 9/00* (2006.01)
*G06T 7/00* (2017.01)
(Continued)

(52) U.S. Cl.
CPC .......... *G06T 7/0012* (2013.01); *G06T 7/0016* (2013.01); *A61B 3/102* (2013.01);
(Continued)

(58) Field of Classification Search
USPC ....... 382/100, 103, 128–134, 154, 162, 168, 382/173, 181, 219, 224, 232, 254, 274,
(Continued)

(56) References Cited

U.S. PATENT DOCUMENTS

2004/0184647 A1 9/2004 Reeves et al.
2008/0312552 A1 12/2008 Zhou et al.
(Continued)

FOREIGN PATENT DOCUMENTS

| EP | 2 372 645 A2 | 10/2011 |
| EP | 2 497 409 A1 | 9/2012 |
| WO | WO 2008/050222 A2 | 5/2008 |

OTHER PUBLICATIONS

Abrámoff et al., "Retinal Imaging and Image Analysis", IEEE Reviews in Biomedical Engineering, vol. 3, 2010, pp. 169-208.
(Continued)

*Primary Examiner* — Seyed Azarian
(74) *Attorney, Agent, or Firm* — Birch, Stewart, Kolasch & Birch, LLP

(57) ABSTRACT

In the context of a method for the analysis of image data representing a three-dimensional volume (10, 20) of biological tissue, for each of a number of subvolumes at least two error probability values (41, 42, 43, 44) are generated, each of the values (41, 42, 43, 44) indicating a probability of a type of imaging error, the totality of subvolumes constituting the three-dimensional volume (10, 20). A single consolidated error probability value (51) is determined for each of the number of subvolumes, based on the at least two error probability values (41, 42, 43, 44). Subsequently, the image data is analyzed to obtain a physiologically relevant conclusion applying to a plurality of subvolumes, weighting in the analysis the image data of a given subvolume of the plurality of subvolumes according to the consolidated error probability (51) of the subvolume.

15 Claims, 4 Drawing Sheets

(51) Int. Cl.
*A61B 3/14* (2006.01)
*A61B 3/10* (2006.01)

(52) U.S. Cl.
CPC ............... *G06T 2207/10101* (2013.01); *G06T 2207/20076* (2013.01); *G06T 2207/30041* (2013.01); *G06T 2207/30168* (2013.01)

(58) Field of Classification Search
USPC .................. 382/276, 286–291, 305; 345/424; 600/425; 351/205, 206; 378/4, 21
See application file for complete search history.

(56) References Cited

U.S. PATENT DOCUMENTS

| | | | |
|---|---|---|---|
| 2011/0267340 A1 | 11/2011 | Kraus et al. | |
| 2012/0127427 A1 | 5/2012 | Guo et al. | |
| 2012/0184845 A1* | 7/2012 | Ishikawa | A61B 3/102 |
| | | | 600/425 |
| 2012/0219200 A1 | 8/2012 | Reeves et al. | |
| 2012/0236259 A1* | 9/2012 | Abramoff | A61B 3/12 |
| | | | 351/206 |
| 2012/0274896 A1* | 11/2012 | Vermeer | A61B 3/102 |
| | | | 351/205 |
| 2014/0002441 A1 | 1/2014 | Hung et al. | |
| 2014/0218363 A1* | 8/2014 | Dastmalchi | A61B 3/102 |
| | | | 345/424 |

OTHER PUBLICATIONS

Dufour et al., "Graph-Based Multi-Surface Segmentation of OCT Data Using Trained Hard and Soft Constraints", IEEE Transactions on Medical Imaging, vol. 32, No. 3, Mar. 2013, pp. 531-543.
Tan et al., "Detection of Macular Ganglion Cell Loss in Glaucoma by Fourier-Domain Optical Coherence Tomography", Ophthalmology, vol. 116, No. 12, Dec. 2009, pp. 2305-2314.e2.

* cited by examiner

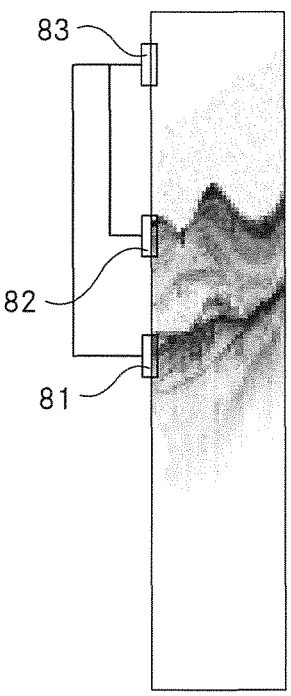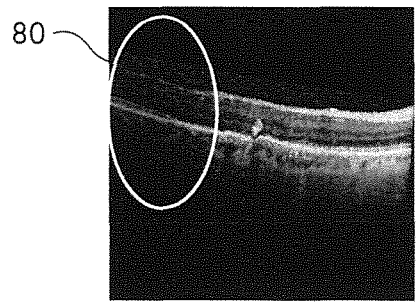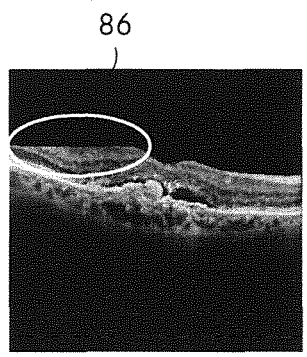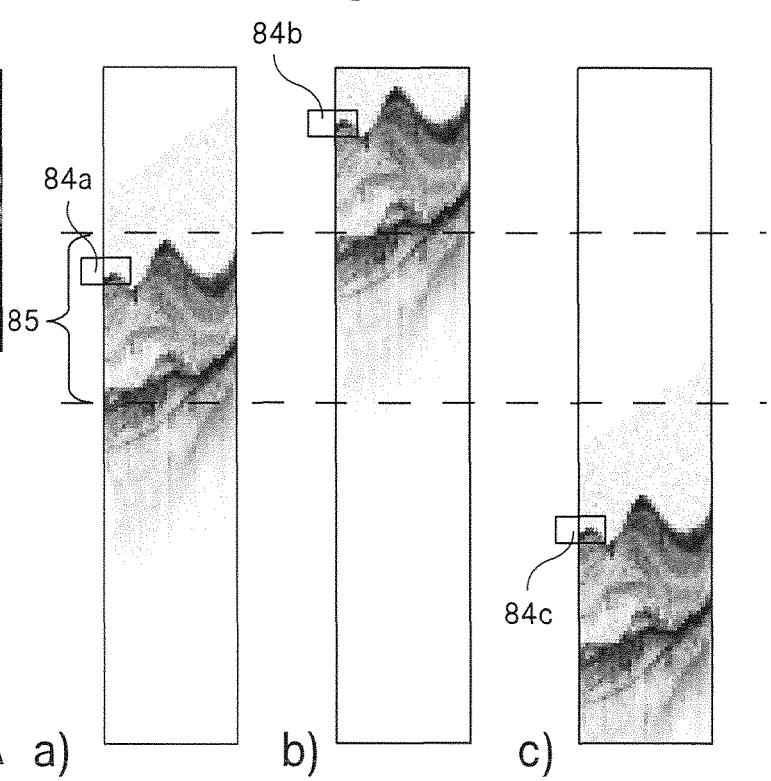
Fig. 4A   Fig. 4B
Fig. 5B
Fig. 5A   a)   b)   c)

METHOD FOR THE ANALYSIS OF IMAGE DATA REPRESENTING A THREE-DIMENSIONAL VOLUME OF BIOLOGICAL TISSUE

TECHNICAL FIELD

The invention relates to a method for the analysis of image data representing a three-dimensional volume of biological tissue. The invention further relates to a computer program for the analysis of image data representing a three-dimensional volume of biological tissue.

BACKGROUND ART

Age-related Macular Degeneration (AMD) and especially neovascular AMD (nAMD) is the leading cause of blindness in the developed countries in people ageing over 50 years. An increase in vascular permeability leads to abnormal fluid collection within or below the retina that causes visual dysfunction when it involves the centre of the macula. This leads to rapidly deteriorating acuity, scarring of the pigment epithelium, and permanent visual loss or blindness.

However, intravitreal injection of antiangiogenic agents, including Ranibizumab (trade name Lucentis®, Novartis, Basel, Switzerland), has been shown to significantly improve the course of nAMD. To reduce the burden of intravitreal injections and to optimize the risk/benefit profile, the progression of nAMD features can be monitored non-invasively by Optical Coherence Tomography (OCT). Prominent nAMD features involve the increase of the thickness of retinal structures. Such an increase may be identified when visually comparing two OCT images of the same region of the retina taken at different times, the temporal distance being several days to several months.

For instance, patients treated with Ranibizumab usually undergo an OCT examination every month. If a significant growth in nAMD features is observed, then a treatment decision is indicated: the patient receives a Ranibizumab injection that day, one month later and two months later (treatment phase). Retreatment can be indicated one month later if the nAMD features have not completely receded. Otherwise, the patient does not receive an injection that day, but regularly indicated maintenance injections (maintenance phase).

The OCT acquisition and the subsequent analysis of OCT acquisitions are usually done by skilled personnel, including ophthalmologists. This means that the monitored patients are required to visit a medical practice or specialized unit of a hospital each time an OCT is to be acquired. This puts a considerable burden upon the patients. Furthermore, the frequency of the OCT acquisitions (such as 1 month) is already sort of a compromise between on one hand close monitoring of the development of nAMD and on the other hand the costs and the burden on the patient.

In principle, automatic analysis of OCT acquisitions may alleviate these problems. In recent years, many algorithms have been designed to automatically analyze OCT acquisitions of the retina, cf. Abràmoff MD, Garvin M., Sonka M., *Retinal Imaging and Image Analysis*, IEEE Rev Biomed Eng. 2010; 3:169-208. In the context of automatic analysis, it is crucial to detect possible imaging errors in order to avoid false negative of false positive results that are exclusively or primarily due to imaging errors. Usually, the signal-to-noise ratio has been employed to provide a measure for the imaging quality. However, this quantity alone usually is not a reliable measure for assessing the reliability of the results of the automatic analysis of the imaging data.

SUMMARY OF THE INVENTION

It is the object of the invention to create a method for the analysis of image data pertaining to the technical field initially mentioned, that allows for reliably assessing the suitability of imaging data for automatic analysis.

The solution of the invention is specified by the features of claim 1. According to the invention the method comprises the steps of:

a) for each of a number of subvolumes generating at least two error probability values, each of the values indicating a probability of a type of imaging error, the totality of subvolumes constituting the three-dimensional volume;

b) determining a single consolidated error probability value for each of the number of subvolumes, based on the at least two error probability values;

c) analyzing the image data to obtain a physiologically relevant conclusion applying to a plurality of subvolumes, weighting in the analysis the image data of a given subvolume of the plurality of subvolumes according to the consolidated error probability of the subvolume Accordingly, an inventive computer program for the analysis of image data representing a three-dimensional volume of biological tissue comprises computer program code adapted to perform the aforementioned steps when run on a computer.

The inventive method allows for the generation of local error probability values, based on at least two types of imaging errors. Using two types enhances the quality of the error prediction. Having local values allows for differently weighting the image data relating to the different subvolumes, depending on the reliability of the image data. It is not always necessary to repeat the imaging step if an error is detected, but if the error affected the image data only locally, it is possible to obtain a physiologically relevant conclusion on the basis of the unaffected image data.

In particular, the plurality of subvolumes taken into account for obtaining the physiologically relevant conclusion fill the entire three-dimensional volume of biological tissue that is to be examined. Furthermore, the same subvolumes may be employed for the determination of the local error probability values and for the analysis of the image data to obtain the physiologically relevant conclusion.

In particular, the image data is optical coherence tomography (OCT) image data. In the case of OCT scans the subvolumes preferably correspond to A-scans (in ultrasound terminology) at a certain position. In the following, the depth axis, the A-scans extend along, is denoted by y, the two axes perpendicular to the y axis, indicating the position of the A-scan, are denoted by x and z, respectively. In particular, the 3-D OCT image data is obtained from spectral-domain OCT.

The method is especially beneficial in the context of automated analysis of large numbers of images. Besides its efficiency it provides an operator-independent assessment, which may be very useful in applications in a reading centre or provided as a service of a database backbone.

In principle, the inventive method may be applied to 3-dimensional image data obtained from other imaging techniques such as angiography, computer tomography etc.

The inventive method is particularly well suited for the study of human or mammalian retina tissue. In particular, it may automatically provide a reliable assessment of the probability of imaging errors in OCT images of the retina.

The invention is not restricted to the study of retina tissue. Other biological tissues may be studied using the inventive method.

In a preferred embodiment of the inventive method, subvolumes of the plurality of subvolumes having a consolidated error probability value exceeding a threshold are excluded from the analysis of the image data to obtain the physiologically relevant conclusion. Thus, the method is simplified and subvolumes where an imaging error is probable do not contribute to the physiologically relevant conclusion at all.

Alternatively, essentially all subvolumes may be taken into account when analyzing the image data. In that case, the corresponding weights are based on the local consolidated error probability values. There exist many possibilities for the assignment of weights, weighting subvolumes having lower error probabilities more than subvolumes having higher probabilities is essentially the only condition for obtaining a reliable result.

Depending on the used imaging technology and the examined biological tissue, a number of possible and suitable sets of error probability values exist. Preferably, the at least two error probability values comprise a first probability value related to a noise-to-signal ratio in the relevant subvolume. Despite the fact that the signal-to-noise (or noise-to-signal) ratio alone is not a reliable quantity to assess the suitability for automated analysis, it is still valuable information when combined with other quantities. Inter alia, the noise-to-signal ratio will substantially increase if there is a local unwanted attenuation of a signal, e. g. due to a misalignment of an imaging beam, as this will lead to a substantially decreased signal.

For calculating the first probability value, preferably a first intensity distribution of image data representing a first region of a given subvolume and a second intensity distribution of image data representing a second region of the given subvolume are determined, where the first region and the second region relate to different functional areas of the biological tissue. Subsequently, the first probability value for the given volume is obtained from comparing the first and the second intensity distribution. Especially in the context of OCT acquisitions there may be areas of the biological tissue that do not substantially backscatter the reference beam ("dark areas"), accordingly, most of the signal received with respect to these areas may be attributed to noise. A comparison of the intensity distribution in these areas with the intensity distribution in a bright region showing a lot of detail information in the OCT image allows for assessing the noise-to-signal ratio.

As an example, in the case of OCT imaging of retina tissue, a suitable dark area will be the vitreous humor, whereas bright areas are located behind the retinal pigment epithelium (RPE) and the inner limiting membrane (ILM). Correspondingly, it is preferred to obtain two measures by comparing the intensity distribution of these two areas to that of the vitreous humor. To be on the safe side, the measure relating to the higher signal-to-noise ratio will be used as a basis for the first probability value.

The intensity distributions may be compared by employing a Kolmogorov-Smirnov test applied to the two distributions. This will yield a quantity related to the difference or separation between the two distributions, its value lying in the range of (0, 1), where 0 denotes identity of the distributions. The complement to 1 may be used as the first probability value.

Other (known) methods for comparing two intensity distributions or for estimating the noise-to-signal ratio may be employed.

Preferably, the at least two error probability values comprise a second probability value indicating a probability that a region of the biological tissue to be examined is not represented by the relevant subvolume. This means that it allows to detect if a tissue region that should be covered by a given subvolume is not covered, e. g. due to a faulty alignment of the imaging device or a corresponding error in the imaging process. This usually leads to gaps in the imaged three-dimensional volume and therefore constitutes an error that should be avoided.

In the case of OCT retinal images it is usually required that the entire retina depth is covered by a given A-scan. If there is a misalignment it may happen that a front part of the retina close to the ILM or a back part of the retina close to or behind the RPE is not covered. In order to obtain the second probability value it is thus feasible to detect the ILM and/or RPE by known segmentation techniques, e. g. by using a graph-cut based algorithm. Then, the position of the ILM and/or RPE with respect to the image boundaries is determined. If this position is close to the boundary, an imaging error is probable and the second probability value will obtain a high value. In order to transform the measured distance to a probability value, a Gauss kernel may be employed.

In preferred embodiments of the inventive method, the subvolumes of the image data representing the three-dimensional volume of biological tissue are obtained by a number of scans of an imaging device, the totality of scans covering the three-dimensional volume. In this case, the at least two error probability values preferably comprise a third probability value indicating a probability of having a discontinuity between neighbouring subvolumes obtained in different scans. Discontinuities may occur if a fixed alignment of the imaging device and of the examined biological tissue is lost. It is much less probable that there is a substantial discontinuity between neighbouring subvolumes of the same scan (e. g. adjacent A-scans of a given B scan) than between neighbouring subvolumes of different scans (e. g. spatially adjacent A-scans of two different B scans), because the temporal offset in the latter case is much bigger than in the first case.

For calculating the third probability value, preferably the neighbouring subvolumes are compared by creating a distance matrix from image data of a succession of voxels of a first of the neighbouring subvolumes in a predefined direction and image data of a succession of voxels of a second of the neighbouring subvolumes in the predefined direction and by calculating the third probability value based on an analysis of the distance matrix.

The distance matrix may be analysed by obtaining a warping function corresponding to a path linking a predetermined start point with a predetermined end point of the distance matrix, a sum of distances given by the distance matrix being minimal along the path. The shortest distance may be determined by employing a pathfinding algorithm known as such, e. g. the Dijkstra algorithm.

This approach is inspired by the "dynamic time warping" method known from the analysis of temporal sequences, e. g. in speech recognition. The warping function corresponds to an optimal match between the voxels of the first subvolume and the voxels of the second subvolume. Discontinuities between the two compared subvolumes will lead to characteristic changes of the path represented by the warping function. This will be apparent if this path is compared to a reference path. In the case of studying retina tissue, the start point along the predefined direction will correspond in particular to the inner limiting membrane of the retina, the end point will correspond to the choroid.

Other methods may be employed. As an example, the position of the ILM may be determined by image analysis, e. g. by a graph-cut based algorithm. A comparison of the ILM position along the y axis then allows for the detection of discontinuities.

Preferably, the at least two error probability values comprise a fourth probability value indicating a probability that the image data representing the relevant subvolume is substantially empty. This may happen because of misalignments of the imaging optics or other optical, mechanical or electronical problems of the imaging device. The image data is considered to be substantially empty if the image intensity is within a narrow range for the entire subvolume. As an example, the fourth probability value may be assigned a value of 1 if the image intensity is below a certain lower threshold for the entire subvolume (e. g. in the lowest 3 or 5% of the intensity value range). Otherwise, the fourth probability value will be assigned a value of 0. Gradated values are also possible.

In a preferred embodiment of the inventive method, especially in the context of OCT retina imaging, all aforementioned error probability values are employed, i. e. values in connection with:
a) noise-to-signal ratio;
b) region of the biological tissue to be examined not represented by the relevant subvolume;
c) discontinuity between neighbouring subvolumes; and
d) image data representing the relevant subvolume being substantially empty.

Preferably, the single consolidated error probability value is determined by application of a machine learning algorithm to the at least two error probability values. A preferred algorithm is support vector regression (SVR). Using a machine learning algorithm allows for systematically including the knowledge of specialists in the field of analysis of the respective image data.

The inventive method is especially useful if two images shall be compared, i. e. the image data comprises a first image representing the three-dimensional volume at a first point in time and a second image representing the volume at a second point in time being different from the first point in time, and where the method includes the step of obtaining at least one local measure for a probability of growth of a layer of the biological tissue along a predefined direction. The tissue or an examined part thereof is represented by a first subvolume of the first image and a second subvolume of the second image, the first subvolume and the second subvolume representing a same region of the three-dimensional volume.

A possible application is the automatic study of the growing of individual layers of the retina, notably in the macula region. The processed data facilitates the detection of nAMD features and provides information that is useful for deciding on further treatment of nAMD. The method therefore may be used as a decision support tool to help clinicians assess the need for intravitreal injections. However, the invention is not restricted to the study of retina tissue. Other biological tissues may be studied using the inventive method, in particular if thickness changes in these tissues over time are of interest. The inventive method of obtaining local error probabilities allows for excluding false alarms and allows for using a maximum number of images, even those affected by local errors.

In such methods, at least two error probability value pairs are generated for a region of the three-dimensional volume represented by the first and second subvolume, each pair comprising an error probability value for the first subvolume and a respective error probability value for the second subvolume. This allows for simultaneously taking into account errors in both images, furthermore, it is possible to compare the error probabilities of the two images, a substantial difference indicating possible problems with at least one of the images.

Preferably, a single local error probability value is obtained from each error probability value pair. This single value is a measure for the probability that the comparison of the given subvolume of the two images is affected by imaging errors, i. e. it directly relates to the physiologically relevant quantity that is to be determined.

In a preferred embodiment of the method it comprises a further step of alerting a user of an imaging device if a total quality of the image data obtained from the consolidated error probability values falls below a threshold. This allows for repeating the imaging step in order to obtain image data that is better suited for automatic analysis. Preferably, the determination of the consolidated error probability values and the assessment of the total image quality are effected in quasi real time such that the user (which may be the patient itself or a healthcare professional) receives immediate feedback. The threshold may be a fixed value to which a quantity obtained from the consolidated error probability values (e. g. the sum, an average or median value) is compared. Alternatively, a machine learning algorithm, e. g. a Support Vector Classification (SVC) model, may be used to classify between "suitable for automated analyses" and "not suitable for automated analysis".

Other advantageous embodiments and combinations of features come out from the detailed description below and the totality of the claims.

BRIEF DESCRIPTION OF THE DRAWINGS

The drawings used to explain the embodiments show:

FIG. 4A, B extracts of OCT images for illustrating a method for the determination of the noise-to-signal ratio;

FIG. 5 an extract of an OCT image for illustrating a method for the determination of missing elements of the biological tissue in the analyzed image;

In the figures, the same components are given the same reference symbols.

PREFERRED EMBODIMENTS

Figure 1:
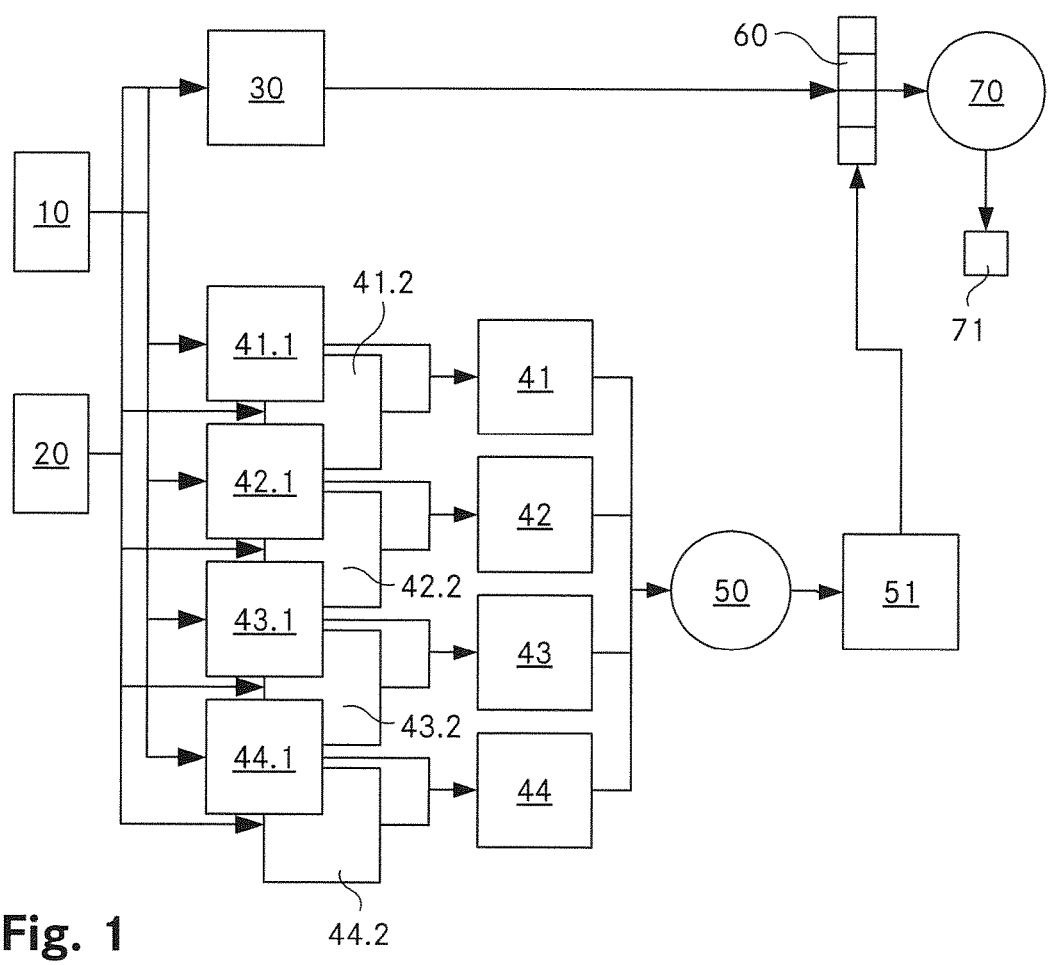
FIG. 1 A schematic representation of the basic steps of a method for the analysis of image data according to the invention.

The FIG. 1 is a schematic representation of the basic steps of a method for the analysis of image data according to the invention. The described method is applied to compare two images 10, 20 of biological tissue taken at two different points in time. The two three-dimensional images 10, 20 are compared to each other in order to obtain a two-dimensional difference map 30, constituted by a grid of values relating to the difference between the image data of respective subvolumes. It provides information about the magnitude of structural change in the given subvolume between the first and the second point in time. Local probabilities for imaging errors in the different subvolumes are calculated and constitute an error probability map 51. This map is taken into account when calculating a (global) feature vector 60 from the difference map 30. Finally, this feature vector 60 is mapped to a desired global quantity (e. g. a global growth probability 71) using a machine learning algorithm.

In the following, the method will be described with reference to 3-D OCT images obtained by spectral domain OCT, taken from the macula region of the human retina. However, the basic steps of the method may be applied to other 3-dimensional images of biological tissue alike.

Figure 2:
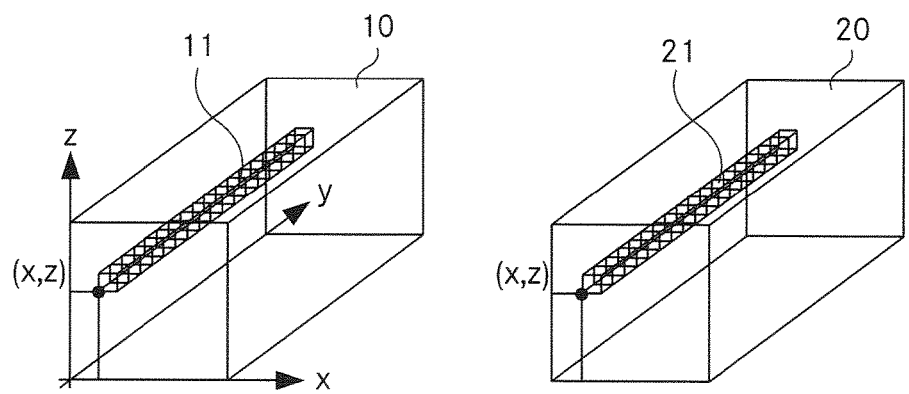
FIG. 2 a schematic representation of a volume of biological tissue represented by image data at two different points in time, including a subvolume to be analysed by an inventive method.

The FIG. 2 is a schematic representation of a volume of biological tissue represented by image data at two different points in time, including a subvolume to be analysed by an inventive method. First of all, the two images 10, 20 representing essentially the same volume of the given tissue, taken at different points in time, e. g. with a temporal distance of 30 days, are obtained. The images are composed of a number of voxels that are arranged in a regular grid, the directions along the grid being denoted by x, y, and z, respectively. The two images 10, 20 are approximately registered in the coronal plane, i. e. in the x-z plane, this may be achieved with today's OCT acquisition devices, e. g. by those featuring fundus SLO tracking (developed by Heidelberg Engineering). The y-axis is the depth axis and runs perpendicular to the coronal plane.

In the given example, both volumes are subsampled to 49×49×496 voxels in order to make the data isotropic in the (x, z) plane. It is to be noted, that the two volumes are not necessarily registered in depth, i.e. along the y-axis. Therefore, the Inner Limiting Membrane (ILM) is segmented in both volumes, using a graph-cut based algorithm, described in Dufour P A, Ceklic L, Abdillahi H et al., *Graph-based multi-surface segmentation of OCT data using trained hard and soft constraints*, IEEE Trans Med Imaging. 2013; 32:531-43. Other known algorithms may be used for that purpose. Then, for the subsequent analysis all A-scans are shifted along the y-axis in order to set the ILM to the y=0 coordinate.

When aligning two A-scans from consecutive acquisitions, direct comparison of voxel intensities is not reliable due to illumination and noise variations between acquisitions. As a first preprocessing step, a median filter of unit radius is thus applied to remove the noise. As a second preprocessing step, a gradient filter is applied to enhance the borders of the main retinal features (interface between retinal layers, borders of the nAMD features, etc.).

The 3-D images are compared A-scan per A-scan, i.e. the A-scan 11 at coordinate (x, z) in the volume represented by the first image 10 is obtained and the A-scan 21 at coordinate (x, z) in the volume represented by the second image 20 is obtained. Both A-scans 11, 21 are subvolumes of the volumes represented by the images 10, 20 and consist of a linear succession of voxels having coordinates (x, y, z), where x and z are constant (and identical for the subvolumes compared to each other) and where the main extension of the A-scans 11, 21, i. e. of the subvolumes, is in the y-direction. The A-scans 11, 21 are then compared to each other as described in more detail below. The result is the difference map 30 which is constituted by a grid of values relating to the difference between the image data of respective subvolumes of the two images 10, 20.

For each of the subvolumes 11, 21 of both images 10, 20 four different error probability values are determined, their totality being represented by eight two-dimensional error maps 41.1, 41.2; 42.1, 42.2; 43.1, 43.2; 44.1, 44.2. The determination of the values is described in more detail below. However, in general the values will be in the range of (0, 1), a high value denoting a higher probability of having an imaging error in the respective subvolume at (x, z). Next, based on each pair of values representing the same type of error probability, obtained from the two images 10, 20, a single local error probability value is obtained, the totality of values is represented by two-dimensional error maps 41, 42, 43, 44. For that purpose, to be on the safe side, the higher of the two values of the value pair will be chosen.

Next, a support vector model based error regression 50 is applied to the error maps 41, 42, 43, 44 yielding a two-dimensional error probability map 51. The elements of this map provide an indication about the probability that a determined structural change at a given position (x, z) is erroneous.

For the error regression 50, a support vector model has been trained using a training dataset of OCT images, assessed by skilled professional ophthalmologists. From the training dataset all pairs of consecutive OCT acquisitions in which a retinal growth was observed by the ophthalmologists have been removed. Assuming that the assessments of the professional observers are perfect, it means that no local retinal growth should be measured in that reduced training set. If nevertheless a local retinal growth has been detected by the algorithm, it was supposedly due to an error in the local retinal growth assessment, probably because of quality issues in the OCT volumes. In fact, the local retinal growths measured in the reduced training set were regarded as error probabilities, given the local quality issues measured at the same location. So, the SVR was trained using the four error values extracted at location (x, z) and stored in error maps 41, 42, 43, 44 as inputs and the local retinal growth measured at location (x, z) as the desired output. There were as many training samples as (x, z) locations in the reduced training set.

Figure 3:
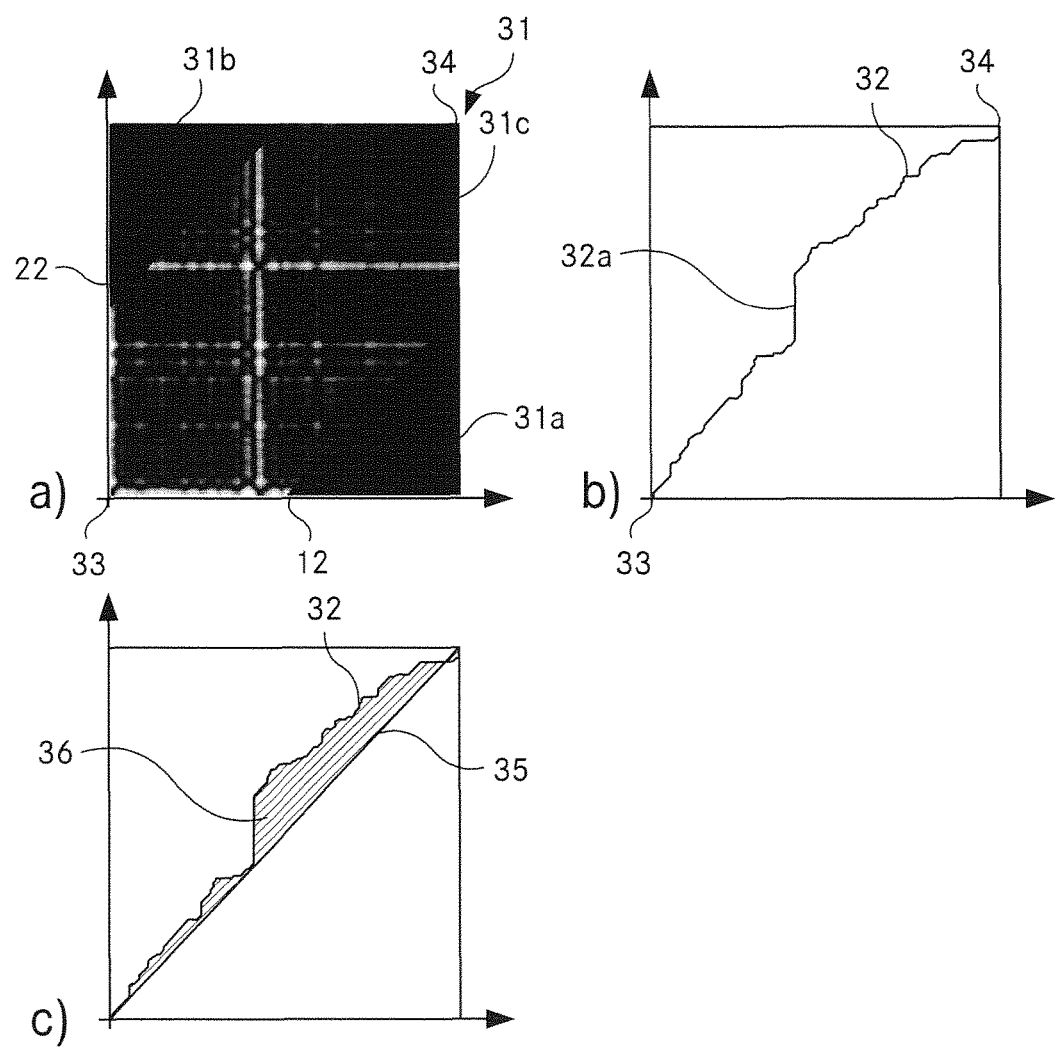
FIG. 3 a) voxel-wise distances with respect to the intensity gradient; b) the shortest distance path corresponding to the voxel-wise distances; c) the area between the shortest distance path and a reference path.

The generation of the difference map 30 is described in connection with FIG. 3.

Based on the filtered images, for each pair of A-scans at a respective (x, z) coordinate the voxel-wise distance with respect to the intensity gradient is determined, i. e. each voxel in the reference A-scan 11 is compared to each voxel in the target A-scan 21, unless their y-coordinates are too distant (thus excluding obviously impossible assignments). The resulting distance matrix 31 is shown in FIG. 3a), where the axes run along the y-coordinate for the reference A-scan 11 ($y_1$ axis 12) and along the y-coordinate for the target A-scan 21 ($y_2$ axis 22): The black triangular areas 31a, 31b at the matrix corners are due to the exclusion of areas where |y1-y2| exceeds a certain threshold. The bright lines 31c in the distance matrix 31 correspond to the enhanced borders of retinal features.

Next, a sequence alignment strategy similar to Dynamic Time Warping (DTW) in signal processing is applied to the two A-scans 11, 21 to be compared. Based on the voxel-wise distance matrix 31, the minimal distortion path 32 between the two A-scans 11, 21, from the ILM 33 (bottom left corner) to the choroid 34 (top right corner) is found, using the well-known Dijkstra algorithm in the graph associated with the voxel-wise distance matrix 31. The resulting path 32 is shown in FIG. 3 b) in the same coordinates as FIG. 3 a). It is the path leading from the ILM 33 to the choroid 34 where the sum of voxel-wise distance values given by the distance matrix 31 along the path is minimal.

If one voxel in the first A-scan is paired with multiple voxels in the second A-scans, it probably means that the tissue recorded in that voxel has grown between the two acquisitions or that fluid has appeared right below or above that voxel. As can be seen from FIG. 3 b), this situation is given in region 32a of the path 32. It is to be noted that the use of the gradient filter enforces the main retinal layers to be aligned in the minimal distortion path 32.

A path running along the diagonal 35 of the distance matrix 31 corresponds to the situation of identical images (no change). A minimal distortion path 32 going above the diagonal 35 indicates that a retinal growth is detected. Therefore, the area 36 above the diagonal 35 and below the minimal distortion path 32 is used as a local retinal growth score, see FIG. 3c), which again employs the same coordinates as FIGS. 3 a) and 3 b).

The aforementioned steps are repeated as long as not all (x, z) coordinates have been analyzed.

Next, based on the local retinal growth scores for each (x, z), the difference map 30, in the present case a growth map, is established by repeating the aforementioned steps. The difference map 30 basically indicates the value of the local retinal growth score s (x, z) as a function of the x- and z-coordinates, i. e. depending on the position on the coronal plane.

Next, a global growth probability for the consecutive volumes is calculated. For that purpose, a global growth feature vector 60 is extracted from the retinal growth map (difference map 30), taking into account the error probability map 51. This feature vector 60 is constituted as follows:

$$\begin{pmatrix} \sum_{x,z} s(x,z) \\ \sum_{x,z} s^2(x,z) \\ I \\ C \end{pmatrix}$$

Where the first two features simply average the local growth scores s (x, z) (given by the retinal growth map) using either a sum or a sum of squares. The last two features are spatial autocorrelation features, namely Moran's I and Geary's C. The latter two can differentiate dispersed or random local growths (that are likely due to noise) from clustered local growths that are typically observed when nAMD features appear or grow. In order to avoid that the feature vector 60 is affected by imaging errors, only those growth scores s (x, z) will be taken into account which relate to coordinates (x, z) where the value in the error probability map 51 is below a certain threshold (i. e. where an error is improbable).

Finally, this global growth feature vector 60 is mapped to a global growth probability 71 using a Support Vector Classification (SVC) model 70. The SVC also provides an optimal cut-off on the global growth probability. So the algorithm produces binary outputs: 'growth' or 'no growth'. If the output is 'growth', a health professional should carry out additional examinations and finally make a treatment decision.

The SVC algorithm has been trained using a training dataset of OCT images, assessed by skilled professional ophthalmologists. A standard training strategy has been adopted for the SVC model: the parameter values (the optimal soft margin parameter C, the optimal kernel function and the optimal kernel function parameters) have been found by two-fold cross-validation. Then the classifier has been retrained in the entire training set using the optimal set of parameters. There have been as many training samples as (x,z) locations in the training set.

The FIGS. 4A, 4B show extracts of OCT images for illustrating a method for the determination of the noise-to-signal ratio. It is to be noted that for reproduction purposes the OCT image is shown inverted, i. e. the (dark) background is shown white and the foreground is black. In the following, we refer to the properties of the non-inverted image.

In this context, the local intensity distribution in the brightest area 81 adjacent to the RPE and in the brightest area 82 adjacent to the ILM is compared to the intensity distribution in the area 83 representing the vitreous humor. For that purpose, first the RPE and the ILM are detected by known image analysis methods such as graph-cut based algorithms. It is assumed that the brightest areas 81, 82 will lie just below the RPE and the ILM and that the image representing the area 83 of the vitreous humor is mainly noise.

Next, the Kolmogorov-Smirnov algorithm is applied to the two intensity distributions compared to each other, i. e. a given number n of measured intensities $I_{1,i}$, $I_{2,i}$, i=1, . . . , n in the respective regions relating to the same A scan are ordered according to their value in ascending order. Next, the empirical distribution functions are calculated as follows:

$$S_{1,i}(x,z) = \Sigma_{j=1}^{i} I_{1,j}(x,z), S_{2,i}(x,z) = \Sigma_{j=1}^{i} I_{2,j}(x,z)$$

The two functions are compared to each other as follows:

$$d_i(x,z) = |S_{1,i}(x,z) - S_{2,i}(x,z)|, \text{ where}$$

$$d_{max}(x,z) = \sup_i d_i(x,z).$$

This yields two values of $d_{max}$ for each coordinate (x,z), one for the comparison between the area behind the RPE to the vitreous humor and one for the comparison between the area behind the ILM to the vitreous humor. Identical intensity distributions yield a value of $d_{max}=0$, i.e. it may be assumed that small values of $d_{max}$ indicate that the noise-to-signal ratio is high. Accordingly, for each A-scan, the complement of the lower value of $d_{max}$ may be chosen as the element of the error maps 41.1, 41.2, providing a measure for the probability that the respective portion of the image is affected by noise.

The FIG. 4B shows a B scan featuring a region 80 exhibiting an attenuated signal. At the given (x, z) coordinates, the probability values in the respective error map 41.1 or 41.2 will have an increased value.

The FIGS. 5A, 5B show extracts of OCT images for illustrating a method for the determination of missing elements of the biological tissue in the analyzed image. Again, for reproduction purposes the OCT image is inverted, i. e. the (dark) background is shown white and the foreground is black. In the following, we refer to the properties of the non-inverted image.

For that purpose the position of the ILM determined as described above with respect to the image boundaries is taken into account. FIG. 5a) shows the situation where the position 84a is within an allowed range 85, whereas in FIGS.

5b) and 5c) the positions 84b, 84c are in front and behind the allowed range 85, respectively. The measured distance is transformed into a probability by employing a Gauss kernel, a low value of the probability assigned to positions well within the allowed range 85. The probabilities enter the error maps 42.1, 42.2.

The FIG. 5B shows a B scan featuring a region 86 where an area adjacent to the ILM is missing due to a misalignment. At the given (x, z) coordinates, the probability values in the respective error map 42.1 or 42.2 will have an increased value.

Figure 6A:
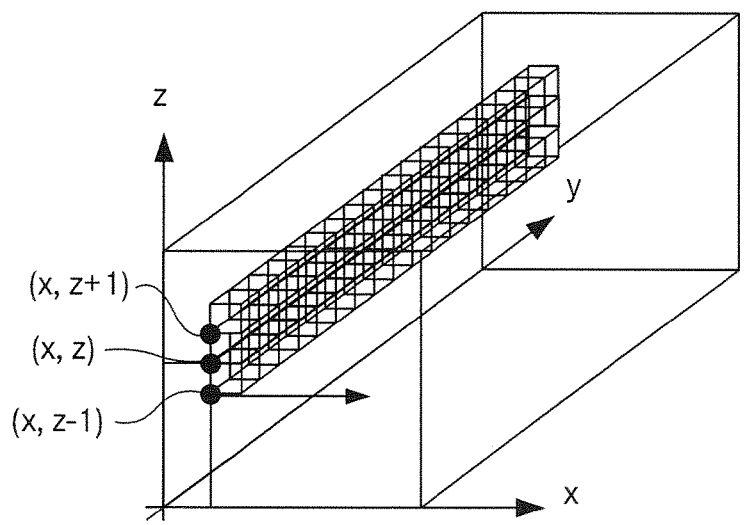
FIG. 6A a schematic representation of three subvolumes of biological tissue represented by image data obtained in subsequent scans.

The 3d OCT image is generated by scanning a beam in the (x,z) plane. In the described example, the beam is scanned along the x axis (scanning direction 87) before its position is incremented in the z direction to obtain a further B scan. This means that neighbouring A-scans separated in the x direction will be separated by a very short time interval, whereas A-scans separated in the z direction (i. e. belonging to different B-scans) are separated by a considerably longer time interval. Accordingly, the risk of having discontinuities between adjacent subvolumes separated in the z direction, such as the three subvolumes at positions (x, z−1), (x, z) and (x, z+1) shown in FIG. 6A, is much bigger than with respect to adjacent volumes separated in the x direction.

If there is no discontinuity between two adjacent subvolumes (A-scans) the intensity distributions will be similar. However, if the relative position between the retina and the imaging device change in between two A-scans, a discontinuity in the intensity distributions arises. Absent other imaging errors, the adjacent A-scans will be very similar but offset with respect to each other in the y direction. This offset is very similar to offsets that arise due to the growth of retinal layers. That is why the method described above for detecting such growing layers may be employed essentially in the same way to detect signal discontinuities as well, based on the preprocessed images without the y-axis alignment according to the ILM position. This method yields a score for each pair of subvolumes, i.e. for the comparison of the subvolumes at (x, z−1) and (x, z) as well as of the subvolumes at (x, z), (x, z+1). The higher the score the bigger the probability that a discontinuity is present, i. e. as long as the value is suitably normalized it may be directly used as the element of the error maps 43.1, 43.2. In order to take into account the discontinuities in both the negative as well as the positive z direction, the average of the scores will be assigned to the element of the map 43.1 or 43.2 with respect to the subvolume at given (x, z).

Figure 6B:
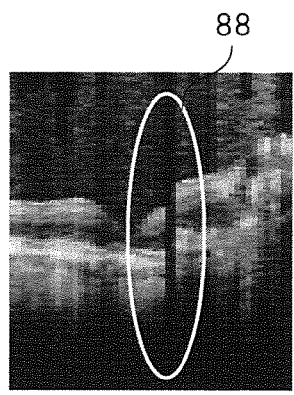
FIG. 6B an extract of an OCT image for illustrating the effect of a discontinuity between subsequent scans.

The FIG. 6B shows an extract of an OCT image for illustrating the effect of a discontinuity between subsequent scans. The extract shows a yz-plane at fixed x, i.e. perpendicular to the usual B scan. It is clearly visible that there is a region 88 exhibiting a discontinuity. At the given (x, z) coordinates, the probability values in the respective error map 43.1 or 43.2 will have an increased value.

The maps 44.1, 44.2 contain values indicating the probability that at a given (x, z) the A-scan is substantially empty, e. g. due to misalignment of the imaging optics or other problems of the imaging device. The image data is considered to be substantially empty if the image intensity is within a narrow range for the entire A-scan at (x, z). In the described example, the fourth probability value is assigned a value of 1 if the image intensity is below a lower threshold of 5 for the entire subvolume (having an intensity resolution of 8 bit). Otherwise, the fourth probability value is assigned a value of 0.

Figure 7:
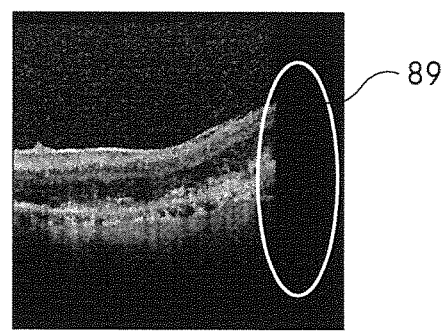
FIG. 7 shows a B scan featuring a region 89 where there is essentially no signal.

The FIG. 7 shows a B scan featuring a region 89 where there is essentially no signal. At the given (x, z) coordinates, the probability values in the respective error map 44.1 or 44.2 will have an increased value.

The invention is not restricted to the aforementioned method. As described above, some steps of the method may be replaced by alternative algorithms. Furthermore, the method is applicable to other tissues and image data stemming from other imaging techniques.

In summary, it is to be noted that the invention creates a method for the analysis of image data that allows for reliably assessing the suitability of imaging data for automatic analysis.

The invention claimed is:

1. A method for the automated analysis of optical coherence tomography image data representing a three-dimensional volume of biological tissue, the method comprising the steps of:
   a) for each of a number of subvolumes generating at least two error probability values, each of the values indicating a probability of a type of imaging error, the totality of subvolumes constituting the three-dimensional volume;
   b) determining a single consolidated error probability value for each of the number of subvolumes, based on the at least two error probability values;
   c) analyzing the image data to obtain a physiologically relevant conclusion applying to a plurality of subvolumes, weighting in the automated analysis the image data of a given subvolume of the plurality of subvolumes according to the consolidated error probability of the subvolume, thereby reliably assessing the suitability of local imaging data for the automated analysis.

2. The method as recited in claim 1, wherein subvolumes of the plurality of subvolumes having a consolidated error probability value exceeding a threshold are excluded from the analysis of the image data to obtain the physiologically relevant conclusion.

3. The method as recited in claim 1, wherein the at least two error probability values comprise a first probability value related to a noise-to-signal ratio in the relevant subvolume.

4. The method as recited in claim 3, wherein a first intensity distribution of image data representing a first region of a given subvolume and a second intensity distribution of image data representing a second region of the given subvolume are determined, the first region and the second region relating to different functional areas of the biological tissue, and in that the first probability value for the given volume is obtained from comparing the first and the second intensity distribution.

5. The method as recited in claim 1, wherein the at least two error probability values comprise a second probability value indicating a probability that a region of the biological tissue to be examined is not represented by the relevant subvolume.

6. The method as recited in claim 1, wherein the subvolumes of the image data representing the three-dimensional volume of biological tissue are obtained by a number of scans of an imaging device, the totality of scans covering the three-dimensional volume, and in that the at least two error probability values comprise a third probability value indicating a probability of a discontinuity between neighbouring subvolumes obtained in different scans.

7. The method as recited in claim 6, wherein the neighbouring subvolumes are compared by creating a distance matrix from image data of a succession of voxels of a first of the neighbouring subvolumes in a predefined direction and image data of a succession of voxels of a second of the neighbouring subvolumes in the predefined direction and by calculating the third probability value based on an analysis of the distance matrix.

8. The method as recited in claim 1, wherein the at least two error probability values comprise a fourth probability value indicating a probability that the image data representing the relevant subvolume is substantially empty.

9. The method as recited in claim 1, wherein the single consolidated error probability value is determined by application of a machine learning algorithm to the at least two error probability values.

10. The method as recited in claim 1, the image data comprising a first image representing the three-dimensional volume at a first point in time and a second image representing the volume at a second point in time being different from the first point in time, the method including the step of obtaining at least one local measure for a probability of growth of a layer of the biological tissue represented by a first subvolume of the first image and a second subvolume of the second image, along a predefined direction, where the first subvolume and the second subvolume represent a same region of the three-dimensional volume.

11. The method as recited in claim 10, wherein least two error probability value pairs are generated for a region of the three-dimensional volume represented by the first and second subvolume, each pair comprising an error probability value for the first subvolume and a respective error probability value for the second subvolume.

12. The method as recited in claim 11, wherein a single local error probability value is obtained from each error probability value pair.

13. The method as recited in claim 1, characterized by a further step of alerting a user of an imaging device if a total quality of the image data obtained from the consolidated error probability values falls below a threshold.

14. The method as recited in claim 1, wherein the biological tissue is human or mammalian retina tissue.

15. A non-transitory computer readable medium having stored thereon a computer program adapted to perform the analysis of image data representing a three-dimensional volume of biological tissue according to the steps of claim 1.

* * * * *